US010605788B2

(12) United States Patent
Tong et al.

(10) Patent No.: US 10,605,788 B2
(45) Date of Patent: Mar. 31, 2020

(54) SAW MAGNETIC SENSOR AND MANUFACTURING METHOD FOR SAME

(71) Applicants: Bei Tong, Shenzhen (CN); Yang Li, Shenzhen (CN); Zhuofan Zhou, Shenzhen (CN); Jun Ouyang, Shenzhen (CN); Benpeng Zhu, Shenzhen (CN)

(72) Inventors: Bei Tong, Shenzhen (CN); Yang Li, Shenzhen (CN); Zhuofan Zhou, Shenzhen (CN); Jun Ouyang, Shenzhen (CN); Benpeng Zhu, Shenzhen (CN)

(73) Assignee: AAC Technologies Pte. Ltd., Singapore (SG)

(*) Notice: Subject to any disclaimer, the term of this patent is extended or adjusted under 35 U.S.C. 154(b) by 464 days.

(21) Appl. No.: 15/383,041

(22) Filed: Dec. 19, 2016

(65) Prior Publication Data

US 2017/0363584 A1 Dec. 21, 2017

(30) Foreign Application Priority Data

Jun. 20, 2016 (CN) .......................... 2016 1 0443415

(51) Int. Cl.
| H01L 41/04 | (2006.01) |
| G01N 29/24 | (2006.01) |
| G01R 33/09 | (2006.01) |
| G01R 33/02 | (2006.01) |

(52) U.S. Cl.
CPC ..... *G01N 29/2462* (2013.01); *G01N 29/2412* (2013.01); *G01N 29/2437* (2013.01); *G01N 29/2468* (2013.01); *G01R 33/02* (2013.01); *G01R 33/095* (2013.01); *G01N 2291/02863* (2013.01)

(58) Field of Classification Search
None
See application file for complete search history.

(56) References Cited

U.S. PATENT DOCUMENTS

| 6,437,668 B1* | 8/2002 | Nakao | H03H 9/25 310/313 B |
| 2002/0059709 A1* | 5/2002 | Takata | H03H 3/10 29/25.35 |
| 2005/0077982 A1* | 4/2005 | Funasaka | H03H 9/02574 333/195 |
| 2007/0183190 A1* | 8/2007 | Eyckmans | B82Y 25/00 365/173 |
| 2008/0314627 A1* | 12/2008 | Fujino | H03H 9/1092 174/256 |

(Continued)

FOREIGN PATENT DOCUMENTS

| CN | 204495981 U | * 7/2015 |
| JP | 6429707 B2 | * 11/2018 |

*Primary Examiner* — J. San Martin
(74) *Attorney, Agent, or Firm* — IPro, PLLC; Na Xu

(57) ABSTRACT

A SAW (Surface Acoustic Wave) magnetic sensor includes: a piezoelectric thin film; a seed layer; an interdigital transducer arranged respectively on each side of the piezoelectric thin film, the interdigital transducer comprising an interdigital electrode made from magnetic materials, and reflector grids located at both ends of the interdigital electrode; an underlying substrate arranged at the seed layer opposite to the piezoelectric thin film. A manufacturing method for the sensor is also disclosed.

9 Claims, 3 Drawing Sheets

(56) References Cited

U.S. PATENT DOCUMENTS

| | | | |
|---|---|---|---|
| 2009/0206844 A1* | 8/2009 | Sabah | G01N 29/02 |
| | | | 324/636 |
| 2012/0256522 A1* | 10/2012 | Ito | G01R 33/0052 |
| | | | 310/313 B |
| 2013/0096825 A1* | 4/2013 | Mohanty | G01C 21/165 |
| | | | 701/472 |
| 2014/0145556 A1* | 5/2014 | Kadota | H03H 9/02228 |
| | | | 310/313 A |
| 2015/0102705 A1* | 4/2015 | Iwamoto | H03H 9/0222 |
| | | | 310/313 B |
| 2016/0003924 A1* | 1/2016 | Sun | G01R 33/093 |
| | | | 324/322 |
| 2017/0077897 A1* | 3/2017 | Otsubo | H01L 41/18 |

* cited by examiner

SAW MAGNETIC SENSOR AND MANUFACTURING METHOD FOR SAME

FIELD OF THE INVENTION

The invention relates to the technical field of magnetic sensors, and more specifically, to a SAW Magnetic Sensor and a manufacturing method thereof.

DESCRIPTION OF RELATED ART

Currently, with the rapid development of information industry, industrial automation, electric and electronic technology, transportation, medical instruments, office automation, household electrical appliances and so on as well as popular use of electronic computer, there exists a huge demand for sensors to transform the tested non-electric parameter into electric signal compatible with computer, thus providing opportunities for the rapid development of magnetic sensor and forming a rather considerable magnetic sensor industry. Traditional magnetic sensor comprises sensors such as those based on Holzer effect, anisotropic magneto resistance effect, giant magneto resistance effect, magneto impedance effect, magnetic induction effect, magneto elastic effect, Faraday effect of electromagnetic induction, fluxgate effect, nuclear magnetic resonance, electron paramagnetic resonance effect, Faraday magneto optic effect and superconducting quantum interference effect.

The SAW magnetic sensor made by compounding of piezoelectric material and magneto elastic material based on magneto-electric effect is a novel type of magnetic detection technology developed in recent years. Chinese Patent Issue No. CN204495981U discloses a SAW Magnetic Sensor based on magneto-electric effect, comprising a piezoelectric thin film, a seed layer provided under the piezoelectric thin film, interdigital transducer provided on the piezoelectric thin film. In the direction far away from the interdigital transducer, the piezoelectric thin film is also provided with magneto elastic thin film, ferromagnetic or anti-ferromagnetic layer and underlying substrate. The ferromagnetic or anti-ferromagnetic layer is located between the magneto elastic thin film and underlying substrate to form a stacking structure. The SAW Magnetic Sensor has a sensor sensitive unit with too many film layer structures, resulting in too many uncontrollable factors and complicated preparation processes.

Therefore, it is necessary to provide an improved SAW Magnetic Sensor to overcome above disadvantage.

BRIEF DESCRIPTION OF THE DRAWINGS

Many aspects of the embodiment can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION OF THE EXEMPLARY EMBODIMENT

The present invention will hereinafter be described in detail with reference to an exemplary embodiment. To make the technical problems to be solved, technical solutions and beneficial effects of present disclosure more apparent, the present disclosure is described in further detail together with the figures and the embodiment. It should be understood the specific embodiments described hereby is only to explain this disclosure, not intended to limit this disclosure.

Figure 1:
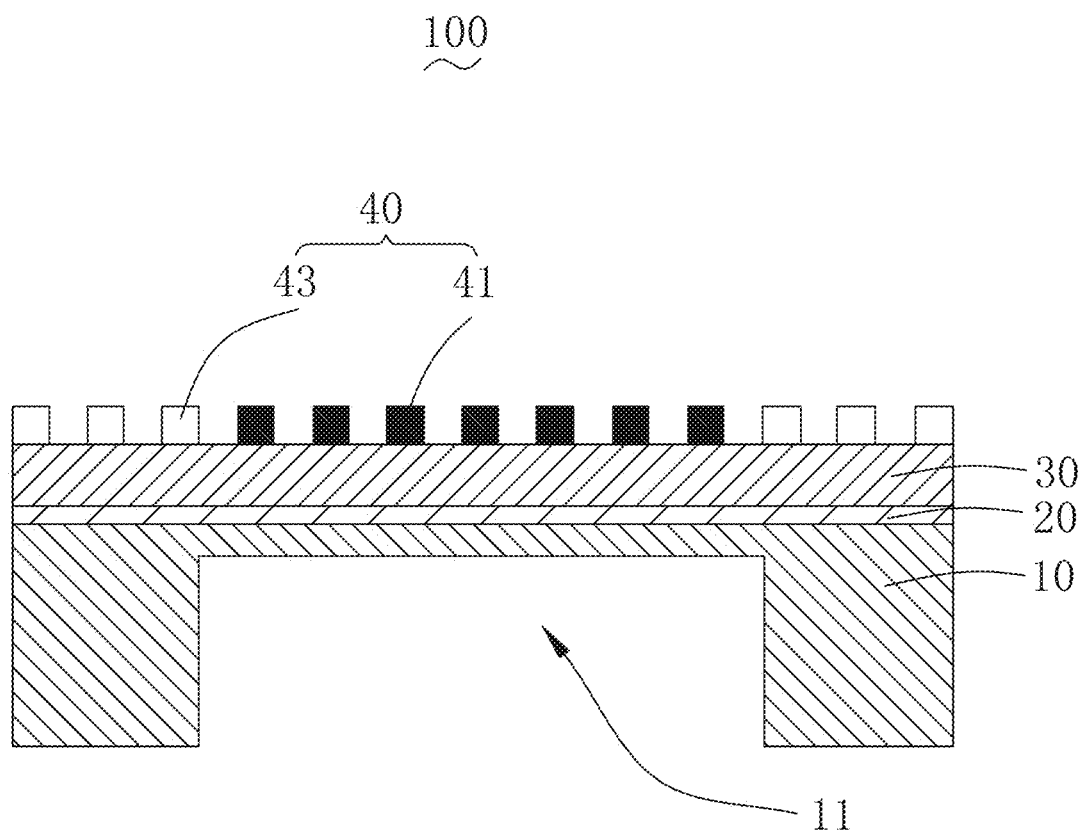
FIG. 1 is a cross-sectional view of a SAW (Surface Acoustic Wave) magnetic sensor in accordance with an exemplary embodiment of the present disclosure.
Figure 2:
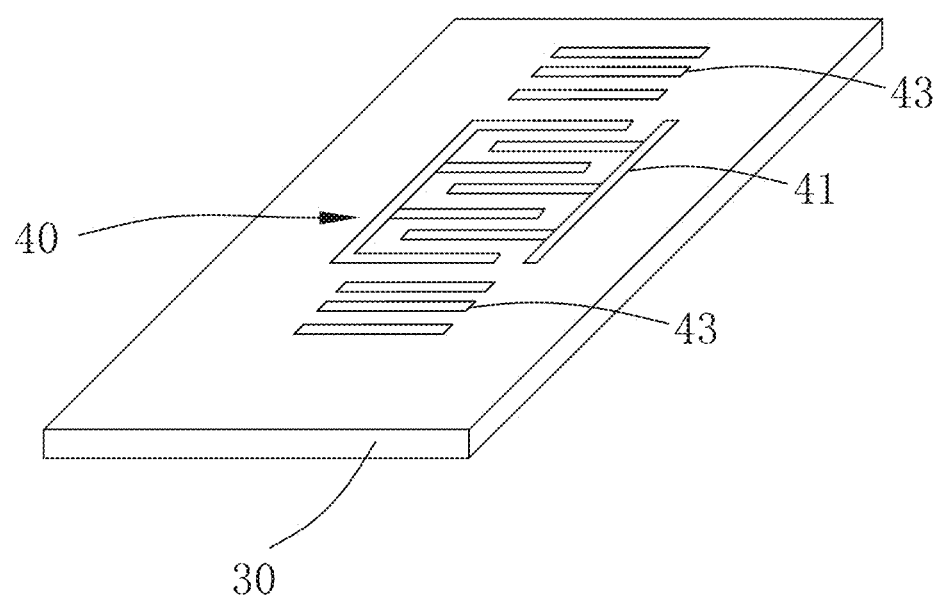
FIG. 2 is an isometric view of a combination of a piezoelectric thin film and an interdigital transduce of the SAW magnetic sensor.

Referring FIGS. 1-2, the SAW magnetic sensor 100 comprises a underlying substrate 10, a seed layer 20, a piezoelectric thin film 30 and a interdigital transducer 40 stacked from bottom to top. The underlying substrate 10 is provided on the lower surface of the seed layer 20 (i.e., the surface of the seed layer 20 far away from the piezoelectric thin film 30), the piezoelectric thin film 30 is provided on the upper surface of the seed layer 20 (i.e., the surface of seed layer 20 far away from the underlying substrate 10), the interdigital transducer 40 is provided on the upper surface of the piezoelectric thin film 30 (i.e. the surface of the piezoelectric thin film 30 far away from seed layer 20).

The underlying substrate 10 is a silicon or silicon dioxide substrate. The underlying substrate 10 comprises a groove 11, the groove 11 is concave from the surface of the underlying substrate 10 far away from the seed layer 20 toward the surface close to the seed layer 20. The groove 11 is formed through etching process.

The material of the seed layer 20 may be one of Mo, Al, Cr, Ti, Pt or Ta, in a thickness of 50 nm~300 nm. The seed layer 20 is provided to be matched with the lattice structure and type of the piezoelectric thin film 30, thus promoting the growth in preferred orientation of the piezoelectric thin film 30 to obtain superior piezoelectric performance.

The material of the piezoelectric thin film 30 is highly oriented AlN, ZnO, LiNiO3 or LiTaO3 and so on, featured by narrow band width, high stability as well as cutting at zero temperature system, less propagation loss with sophisticated technical process. The piezoelectric thin film 30 has a thickness of 200 nm~2000 nm.

The interdigital transducer 40 comprises an interdigital electrode 41 and reflector grids 43 provided at both ends of the interdigital electrode 41, i.e., the interdigital electrode 41 is switched between the reflector grids 43. On the surface of piezoelectric thin film 30, the interdigital electrode 41 forms an interdigital electrode 41 of same period and equivalent finger length in the finger width of one quarter of horizontal shearing SAW wavelength, the period of the interdigital electrode 41 is twice of the finger width of the interdigital electrode 41 or a half of the SAW wavelength. The interdigital electrode 41 is magnetic interdigital electrode, and can be one of a FeCoSiB interdigital electrode, a FeBSiC interdigital electrode, a FeGaB interdigital electrode, a NiFe interdigital electrode, a FeSiB interdigital electrode or a FeCoB interdigital electrode. Magnetic materials such as FeCoSiB, FeBSiC, FeGaB, NiFe, FeSiB, FeCoB are featured by high magnetic permeability, low coercivity and high sensitivity to weak magnetic field. The interdigital electrode 41 has a thickness of 50 nm~300 nm. Interdigital electrode 41 in different thickness has the function of adjusting the speed of interface acoustic wave, the electrode can be trapezoidal or rectangular.

The invention discloses a manufacturing method of the SAW magnetic sensor 100 as below:

Step 1. Provide underlying substrate, clean up and dry the surface of the underlying substrate; the underlying substrate is silicon or silicon dioxide substrate;

Step 2. Sputter to form a seed layer on the surface of the underlying substrate provided in Step 1 by RF magnetron sputtering; the material of the seed layer 20 may be one of Mo, Al, Cr, Ti, Pt or Ta, in a thickness of 50 nm~300 nm;

Step 3. Sputter to prepare the piezoelectric thin film on the surface of the seed layer resulted from Step 2 by RF magnetron sputtering; the piezoelectric thin film material is highly oriented AlN, ZnO, LiNiO3 or LiTaO3 and so on, in a thickness of 200 nm~2000 nm;

Step 4. Prepare the interdigital transducer on the piezoelectric thin film resulted from Step 3, the interdigital transducer comprises the interdigital electrode and the reflector grids located at both ends of the interdigital electrode, the interdigital electrode is a magnetic one; specifically, obtain the pattern of interdigital electrode on the piezoelectric thin film through photo etching process, then obtain the interdigital electrode through etching process, the interdigital electrode is prepared from any one kind of material of FeCoSiB, FeBSiC, FeGaB, NiFe, FeSiB, FeCoB, in a thickness of 50 nm~300 nm;

Step 5. Etch the surface of the underlying substrate far away from the seed layer, form a groove through etching process.

Specifically, steps 1 to 4 finish the preparation of the film layer structure of the SAW magnetic sensor, then etch the surface of the underlying substrate far away from the seed layer, the groove is concave from the surface of the underlying substrate far away from the seed layer toward the surface close to the seed layer.

The SAW magnetic sensor 100 according to the present invention takes use of SAW vibration mode, in the principle based on ΔE effect. As the result of magnetization of test samples, changes in elastic modulus occurs to ferromagnetic metal and alloy, such phenomenon is called ΔE effect. The interdigital electrode 41 according to the present invention is a magnetic one to form ΔE effect, i.e., the ferromagnetic material used for preparing the interdigital electrode 41 has anisotropy, will have changes in elastic modulus of it with the change of polarized magnetic field.

The interdigital electrode 41 is directly provided on the upper surface of the piezoelectric thin film 30, the resonance frequency f of the SAW magnetic sensor is mainly dependent on the elastic modulus and material density of the piezoelectric thin film 30 and the interdigital electrode 41. Resonance frequency $f=(E/\rho\ 1/2/2P$, wherein E represents elastic modulus, ρ represents density, P represents the period of interdigital electrode. In this embodiment, the period of the interdigital electrode 41 is twice of the finger width of the interdigital electrode 41 or a half of the SAW wavelength. Because the interdigital electrode 41 has the function of sensing the external magnetic field, its elastic modulus is relevant with the external magnetic field, i.e. elastic modulus changes under the effect of external magnetic field, and thereby the equivalent elastic modulus of the whole device will also change, thus causing the change in resonance frequency of SAW, so it allows to detect the magnitude of external magnetic field by detecting the change in resonance frequency.

Figure 3:
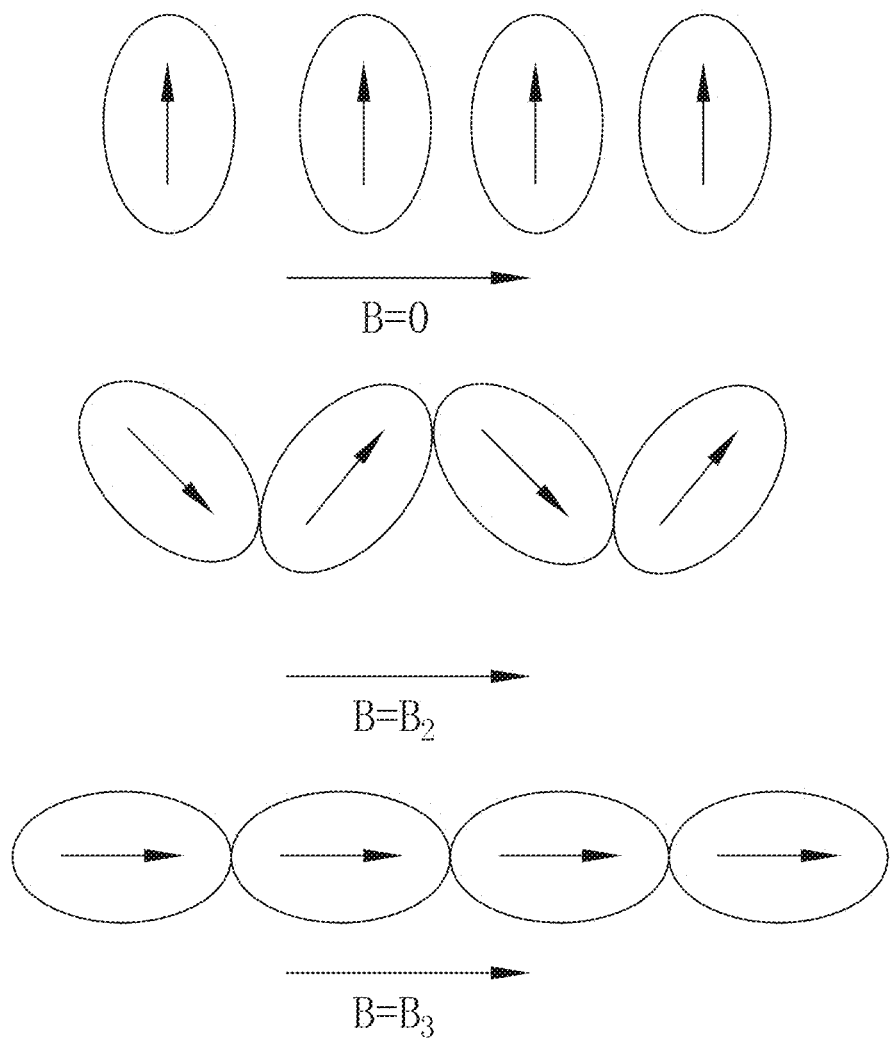
FIG. 3 is an equivalent diagram of the effect of the interdigital transducer of the SAW magnetic sensor shown in FIG. 1 under the effect of bias magnetic field.
Figure 4:
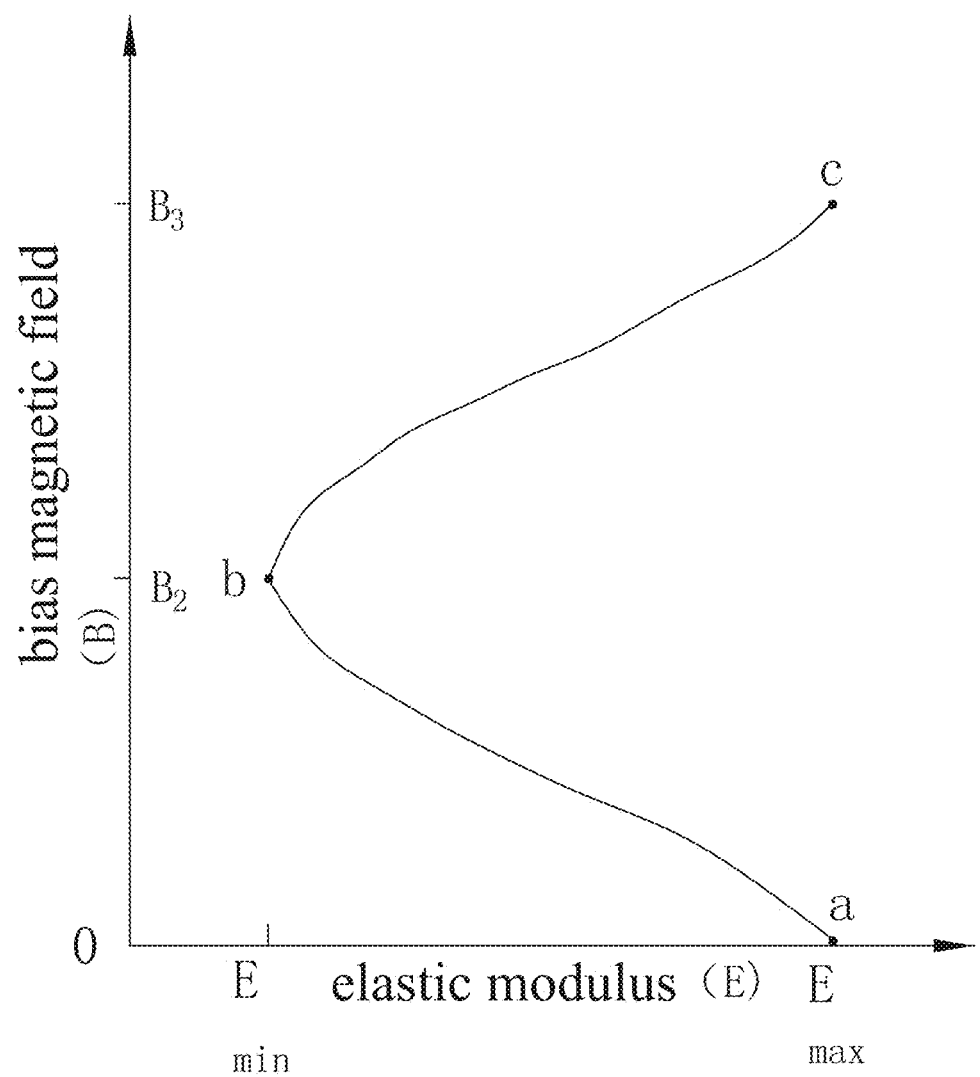
FIG. 4 shows the relationship of the elastic modulus and the bias magnetic field of the interdigital transducer of the SAW magnetic sensor shown in FIG. 3.

Specifically, the elastic modulus of the interdigital electrode has relation with the polarized magnetic field as below:

Referring to FIGS. 3-4, it can be seen in conjunction with FIG. 3 and FIG. 4 that, at the point a, the uniaxial anisotropy of the interdigital electrode is induced by magnetic annealing, i.e. it's divided into Hard axis and Easy axis, when there exists no bias magnetic field (B=0), the elastic modulus has a maximum value Emax. At the point b, by applying a bias magnetic field B2 in the direction of hard axis, this causes the elastic modulus to drop to the lowest Emin, it's a process from point a to point b that its elastic modulus drops gradually with the increase of polarized magnetic field. At the point c, by applying a bias magnetic field B3 (B3>B2) in the direction of hard axis, it causes the elastic modulus to increase to Emax, it's a process from point b to point c that its elastic modulus increases gradually with the increase of polarized magnetic field.

The width direction of the interdigital electrode is the hard axis, the length direction of the interdigital electrode is the easy axis.

In case of applying magnetic field along the direction of Easy axis, it will only cause the rotation of inconsistently aligned magnetic domain without significant changes in elastic modulus.

The interdigital electrode 41 has high shape anisotropy (which means width in micron scale, finger length in millimeter scale, with a difference of one order of magnitude), thereby the interdigital electrode 41 has high magnetic anisotropy correspondingly. By applying magnetic field along the direction of the width of interdigital electrode, i.e. the hard axis, its changes in elastic modulus is significantly bigger than that caused by applying magnetic field along the direction of the length of interdigital electrode, i.e. the Easy axis, in another word, the sensitivity unit is very sensitive to the changes in the magnetic field in the direction of the width of interdigital electrode, while nearly no response to the changes in the magnetic field in the direction of the length of interdigital electrode, which is just the feature required for magnetic sensor to make uniaxial measurement. Thereby, the SAW magnetic sensor according to the present invention has the advantages of high sensitivity, high definition and high anisotropy.

The beneficial effects of the SAW magnetic sensor according to the present invention include: the SAW magnetic sensor 100 measures magnetic field by use of magnetoelectric composite's property of change in resonance frequency with the magnetic field, it has an interdigital electrode 41 which is a magnetic interdigital electrode, prepared from ferromagnetic material, directly stacked on the piezoelectric thin film 30. Under the effect of external magnetic field, the interdigital electrode 41 will have change in its elastic modulus so as to cause change in equivalent elastic modulus of the whole device, resulting in change in the resonance frequency of SAW, so it allows to detect the magnitude of external magnetic field by detecting the change in resonance frequency. The SAW magnetic sensor 100 according to the present invention has a simple film layer structure can simplify the technical process, has the advantages such as low cost, high anisotropy, high sensitivity, high resolution, easiness of miniaturization as well as compatibility with such microelectronics process such as MEMS and CMOS.

It is to be understood, however, that even though numerous characteristics and advantages of the present exemplary embodiment have been set forth in the foregoing description, together with details of the structures and functions of the embodiment, the disclosure is illustrative only, and changes may be made in detail, especially in matters of shape, size, and arrangement of parts within the principles of the invention to the full extent indicated by the broad general meaning of the terms where the appended claims are expressed.

What is claimed is:

1. A SAW (Surface Acoustic Wave) magnetic sensor comprising:
   a piezoelectric thin film;
   a seed layer and an interdigital transducer arranged respectively on each side of the piezoelectric thin film, the interdigital transducer comprising an interdigital electrode made from magnetic materials, and reflector grids located at both ends of the interdigital electrode; and
   an underlying substrate arranged at the seed layer opposite to the piezoelectric thin film.

2. The SAW magnetic sensor as described in claim 1, wherein the magnetic interdigital electrode is one of a FeCoSiB interdigital electrode, a FeBSiC interdigital electrode, a FeGaB interdigital electrode, a NiFe interdigital electrode, a FeSiB interdigital electrode, and a FeCoB interdigital electrode.

3. The SAW magnetic sensor as described in claim 2, wherein the interdigital electrode has a thickness of 50 nm~300 nm.

4. The SAW magnetic sensor as described in claim 1, wherein the period of the interdigital electrode is twice of the finger width of the interdigital electrode or a half of the SAW wave length.

5. The SAW magnetic sensor as described in claim 1, wherein the underlying substrate is silicon or silicon dioxide underlying substrate.

6. The SAW magnetic sensor as described in claim 1, wherein the underlying substrate comprises a groove, the groove is concave from the surface of the underlying substrate far away from the seed layer toward the surface close to the seed layer.

7. The SAW magnetic sensor as described in claim 1, wherein the piezoelectric thin film is made from one of the materials among AlN, ZnO, LiNiO3 or LiTaO3, and has a thickness of 200 nm~2000 nm.

8. A manufacturing method of the SAW magnetic sensor as described in claim 1, comprising the following steps:
   Step 1: Providing an underlying substrate;
   Step 2: Preparing a seed layer by sputtering on the surface of the underlying substrate provided in Step 1;
   Step 3: Preparing a piezoelectric thin film by sputtering on the surface of the seed layer resulted from Step 2;
   Step 4: Preparing an interdigital transducer on the piezoelectric thin film resulted from Step 3, the interdigital transducer comprising an interdigital electrode and reflector grids located at both ends of the interdigital electrode, wherein the interdigital electrode is made from magnetic material.

9. The manufacturing method of the SAW magnetic sensor as described in claim 8, further comprising the step of:
   Step 5: Etching the surface of the underlying substrate far away from the seed layer, and forming a groove through etching process, wherein the groove is concave from the surface of the underlying substrate far away from the seed layer toward the surface close to the seed layer.

* * * * *